United States Patent [19]
Fishman et al.

[11] Patent Number: 5,574,562
[45] Date of Patent: Nov. 12, 1996

[54] METHOD AND APPARATUS FOR EVALUATION OF HIGH TEMPERATURE SUPERCONDUCTORS

[75] Inventors: Ilya M. Fishman, Palo Alto; Gordon S. Kino, Stanford, both of Calif.

[73] Assignee: The Board of Trustees of the Leland Stanford Junior University, Stanford, Calif.

[21] Appl. No.: 359,283

[22] Filed: Dec. 19, 1994

[51] Int. Cl.$^6$ .................................................. C01N 21/55
[52] U.S. Cl. ............................................ 356/432; 356/445
[58] Field of Search .............................. 356/432 T, 432, 356/445, 447, 448

[56] References Cited

U.S. PATENT DOCUMENTS

| | | | |
|---|---|---|---|
| 4,579,463 | 4/1986 | Rosencwaig et al. | 374/57 |
| 4,634,290 | 1/1987 | Rosencwaig et al. | 374/5 |
| 4,636,088 | 1/1987 | Rosencwaig | 356/445 |
| 4,795,260 | 1/1989 | Schuur et al. | 356/400 |
| 5,074,669 | 12/1991 | Olsal | 356/445 |
| 5,110,792 | 5/1992 | Nakayama et al. | 505/1 |
| 5,228,776 | 7/1993 | Smith et al. | 374/5 |
| 5,379,110 | 1/1995 | Matsui et al. | 356/445 |

OTHER PUBLICATIONS

Article by Fishman et al, entitled "Comment on Thermal Transport . . . ", published in Phys. Rev. Lett., 72, 588, (1994).

Article by Fishman et al, entitled "Density of Normal Carriers . . . ", published in Phys. Rev., B 50, 7192, (1994).

Article by Hardy et al, entitled "Precision Measurement of Temperature Dependence . . . ", published in Phys. Rev. Lett, 70,3999, (1993).

Article by Cooper et al, entitled "Optical Studies of the A–,B–,and C-axis Charge Dynamics . . . ", published in Phys. Rev., B 47, 8233, (1993).

Book by Tinkham, M, entitled "Introduction to superconductivity", published by McGraw–Hill, NY, 1975.

*Primary Examiner*—Richard A. Rosenberger
*Attorney, Agent, or Firm*—Bella Fishman

[57] ABSTRACT

A technique for evaluation of high-$T_c$ superconducting films and single crystals is based on measurement of temperature dependence of differential optical reflectivity of high-$T_c$ materials. In the claimed method, specific parameters of the superconducting transition such as the critical temperature, anisotropy of the differential optical reflectivity response, and the part of the optical losses related to sample quality are measured. The apparatus for performing this technique includes pump and probe sources, cooling means for sweeping sample temperature across the critical temperature and polarization controller for controlling a state of polarization of a probe light beam.

27 Claims, 5 Drawing Sheets

METHOD AND APPARATUS FOR EVALUATION OF HIGH TEMPERATURE SUPERCONDUCTORS

This invention was made with Government support under Grant DE-FGO3-90ER14157 awarded by DOE.

FIELD OF THE INVENTION

The present invention relates to optical methods for evaluating high temperature superconducting films and single crystals and apparatus thereof.

BACKGROUND OF THE INVENTION

The evaluation of high temperature superconductors is becoming an important issue for those involved in research and fabrication of these materials. Currently, in spite of great expectations, understanding of basic physics and commercial application of these materials are in very initial stages.

The conventional ways of characterizing high-$T_c$ superconducting materials are to measure their basic properties: critical temperature $T_c$, critical current, heat capacity jump, structural uniformity and imperfections such as impurities, grain and twin boundaries. The jump in heat capacity at the critical temperature is measured in calorimetric experiments and addresses a basic feature of a superconducting transition as a second order phase transition. Critical temperature and critical current are usually determined from temperature dependence of electrical DC or microwave resistance [M. Tinkham, *Introduction to Superconductivity*, McGraw-Hill, N.Y., 1975]. Structural uniformity and imperfections are monitored by X-ray and optical microscopy techniques. Measurements of DC and microwave resistance in zero and non-zero magnetic field are most frequently used because they directly address the manifestations of superconductivity. However, these methods are much less effective for the high-$T_c$ superconducting materials, than for conventional superconductors (metals). The high-$T_c$ superconducting materials are, by nature, very anisotropic and difficult to grow in large volumes. For successful implementation of the traditional methods, (both electrical and thermal), samples of rather large volumes(~1 mm$^3$) and high level of uniformity are required. The current technology is unable to provide uniform single crystals of a size larger than ~1 mm. None of the techniques disclosed above has allowed to evaluate characteristics of small volumes (sample size <100 µm) of high-$T_c$ superconducting materials with required accuracy and sensitivity to the anisotropy and structural defects.

The next approach to the problem has been initiated by development of a photothermal technique which was earlier employed for evaluation of thermal properties of semiconductors, metals and insulating materials. The teaching of the U.S. Pat. Nos. 4,579,463; 4,634,290; 4,795,260; 5,074,669 and 5,228,776 is directed to photothermal measurements of semiconductor wafers. In the techniques disclosed, the surface of the sample is irradiated by light beams of a pump laser and a probe laser, both focused onto the sample surface and separated by a predetermined distance. The intensity of the pump laser beam is periodically modulated which causes heating of a spot on the surface of the sample on which the light beam is focused. The temperature of the spot varies synchronously with the modulation of the pump laser source light beam. The thermal wave excited by the pump source beam propagates along the sample and modulates its dielectric constant. To measure reflectivity, a second probing optical beam is used. The measured AC intensity of the reflected probe beam and the phase delay between the modulation of the incident beam and that of the reflected probe beam are used to obtain the thermal diffusivity of the material. The existing teaching of the photothermal technique neglects the anisotropic optical properties of high-$T_c$ materials and their nonuniformity causing problems for measurements over wide temperature range. In the existing form, the photothermal technique is not suitable for measuring of temperature dependence of thermal and optical parameters of high-$T_c$ materials.

For characterization of high-$T_c$ materials, the existing photothermal technique has to be substantially modified. Strong anisotropy of these materials makes the direction of polarization of the probe beam an important characterization tool. Nonuniformity of the high-$T_c$ samples demands special equipment to control the relative position of samples and the optical means during the measurement cycle, namely to change the direction of polarization of the probe beam relative to the high-$T_c$ sample.

SUMMARY OF THE INVENTION

In the claimed method, specific parameters of the superconducting transition such as the critical temperature and anisotropy of the differential optical reflectivity response are measured. Obtaining these parameters and their polarization dependence, we determine symmetry of the superconducting order parameter. Different spatial symmetry of these optical responses allows for determination of the part of the optical losses related to sample quality. Polarization dependence is used to determine the temperature induced birefringence below $T_c$.

It is an advantage of the present invention to measure anisotropic differential optical reflectivity of superconducting single crystals.

It is a further advantage of the present invention to obtain the crystallographic symmetry and uniformity of high-$T_c$ material by measuring angular dependence of the differential optical reflectivity.

It is a further advantage of the present invention to separate the superconducting and non-superconducting responses of the high-$T_c$ material by analyzing symmetry and anisotropy of the differential optical reflectivity.

It is another advantage of the present invention to optically measure the critical temperature of the superconducting samples, both single crystals and thin films.

It is another advantage of the present invention to optically measure the optical loss difference between the normal and superconducting states and hence the sample quality.

Yet another advantage of the present invention is to provide a suitable apparatus for evaluation of parameters of superconducting films and single crystals.

In accordance with one aspect of the present invention, there is provided a new method and apparatus for evaluation of superconducting samples. The sample surface is periodically heated with a first modulated light beam which is generated by a pump laser. Periodic heating excites a thermal wave propagating through the sample. A second light beam is generated by a probe laser. The probe laser beam is collinearly combined with the pump laser beam and is focused on the sample surface. To investigate the polarization dependence of the obtained signals, retardation plates and polarizers are introduced in the optical beams. Either the non-polarized or polarized component of the reflected probe beam is registered by a detector.

In accordance with another aspect of the present invention, anisotropic differential optical reflectivity of superconducting single crystals is measured. Angular dependence of the differential optical reflectivity is used to distinguish the responses of superconducting and non-superconducting phases of the high-$T_c$ material and analyze symmetry and anisotropy of these responses.

In accordance with another aspect of the present invention, the critical temperature of the superconducting samples is optically measured for single crystals and thin films.

In accordance with another aspect of the present invention, crystallographic symmetry and uniformity of the superconducting sample is measured by defining angular dependence of the differential optical reflectivity and by scanning the sample surface.

In accordance with another aspect of the present invention, the fraction of optical losses related to quality of the superconducting samples is defined by comparison of differential optical responses of normal and superconducting phases.

Yet in accordance with another aspect of the present invention, an apparatus is provided for practical implementation of the proposed method. The apparatus comprises a polarization controller for controlling a state of polarization of an incident light beam generated by a probe laser and directed to the surface of the sample, and analyzing a state of polarization of a light beam reflected from the sample surface. Control of the polarization state is especially important for characterization of anisotropic properties of high-$T_c$ materials. The apparatus also comprises cooling means with the sample of the superconducting material disposed therein and illuminated through the optical window by the pump and probe lasers.

The crucial difference between the teaching of the present invention and the other techniques for the conventional evaluation of superconducting materials is that it is able to characterize very small sample volumes of the order of $10^{-13}$ cm$^3$ due to the fact that we employ new physical effects discovered in our investigations of high-$T_c$ materials. These and other features of the present invention will become clear from the detailed description given below in which a preferred method embodying the present invention and apparatus for implementing this method is described in relation to the drawings. The detailed description is presented to illustrate the present invention, but is not intended to limit it.

BRIEF DESCRIPTION OF DRAWINGS

The invention is described in greater detail herein in terms of a non-limiting embodiment and with reference to the attached drawings, wherein.

DETAILED DESCRIPTION OF THE PREFERRED EMBODIMENT

In this specification, the nature and theoretical concept of the present invention will be disclosed followed by engineering principles which are applicable for evaluation of characteristics of superconducting materials.

With the claimed method, we measure anisotropic differential optical reflectivity (DOR) of superconducting cuprates YBa$_2$Cu$_3$O$_{7-\delta}$ (YBCO), Bi$_2$Sr$_2$CaCu$_2$O$_8$ (BSCCO), etc. in the visible or near infrared spectral region. For the DOR measurements, a periodic thermal excitation of said material is needed. In the preferred embodiment, the temperature variation on a sample surface is caused by an external source producing the light beam partially absorbed by the superconducting material. This light beam is obtained from a pump laser (for example, a laser diode or an Ar ion laser), and the beam intensity is modulated at frequency $\omega$. The pump laser energy absorbed on the sample surface causes the sample heating. Heat propagation inside the sample is described by a diffusion equation for temperature T:

$$\frac{\partial T}{\partial t} = D\nabla^2 T, \qquad (1)$$

where D is thermal diffusivity of the high-$T_c$ sample. The relation between the external energy flux $J_0$ and the sample temperature is defined by the boundary condition:

$$J_0 = -\kappa_0 \frac{\partial T}{\partial x} \qquad (2)$$

where $\kappa_0$ is thermal conductivity. For the external flux periodically varying in time as $\exp(i\omega t)$, the sample temperature acquires a periodic perturbation $\Delta T \sim \theta(x)\exp(i\omega t)$, where the amplitude $\theta(x)$ describes a critically damped thermal wave varying as $\exp(-qx)$ with a wave vector $q=(1+i)\sqrt{\omega/2D}$.

Periodic variation of the sample temperature is detected by measurement of the sample optical reflectivity. To measure the optical reflectivity, the sample is illuminated by a probe laser having wavelength different from the pump laser, and the intensity of the reflected probe light is measured by a detector. Measurements of the conventional optical reflectivity of high-$T_c$ materials in the energy range $\sim 1.5$ eV have shown no specific spectral structure or temperature dependence related to the superconducting transition [S. L. Cooper et al, Phys. Rev. B 47, 8233, 1993]. In the claimed method, the optical response from the high-$T_c$ sample related to the conventional optical reflectivity is suppressed, and a detected periodic component of the reflected probe beam presents only the temperature-dependent portion of the reflectivity dR/dT. This DOR signal presents only the optical transitions between the electron states whose population varies with temperature, and neglects the temperature independent transitions. Close to the critical temperature, the population of some electron states is changing which directly affects the DOR signal.

Figure 1A:
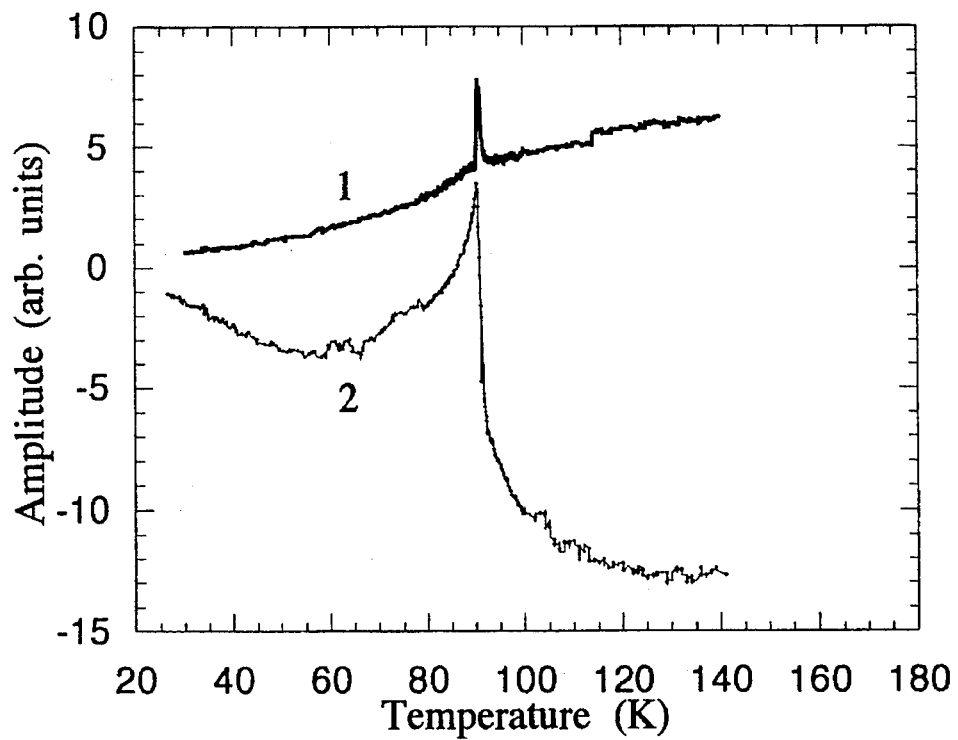
FIG. 1a is temperature dependence of differential reflectivity for the probe beam polarization along the a axis (curve 1) and along the b axis (curve 2) of a single YBCO domain.
Figure 1B:
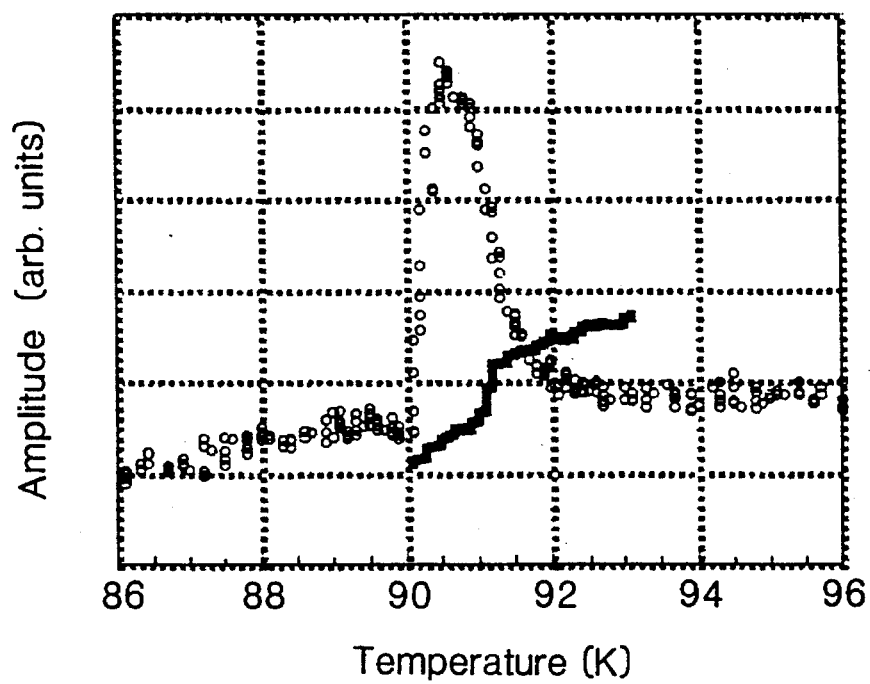
FIG. 1b shows curve 1 in the vicinity of $T_c$ together with the inductive coil response indicating the superconducting transition temperature.

In our DOR measurements of high-$T_c$ materials, we observed several manifestations of superconducting transition in the vicinity of $T_c$. An example of the DOR optical response of YBCO single crystal having single domains of (20×100) μm is shown in FIG. 1. Integration of the DOR signal over temperature indicates that the reflectivity R changes by less than 1% in the temperature range (20–120) K. Because the DOR response of these samples is anisotropic we used a linearly polarized probe beam. The direction of polarization could be changed relative to the sample orientation. Above $T_c$, the sign of the DOR signal is different for the probe polarization along the a (curve 1) and b (curve 2) axes. Examination of FIG. 1 shows that the observed signal can be considered as a sum of two components. One of them gives rise to a sharp peak in the vicinity of $T_c$. The second component is a background signal which varies slowly above $T_c$ and approximately doubles in the temperature range 100–300 K. The peak is shifted about 1 K below $T_c$ (substantially more than the possible average heating caused by the pump and probe lasers separated by ~10 μm). Below ~20 K, both DOR components become indistinguishable from noise.

The power reflection coefficient is $R=|(\sqrt{\epsilon}-1)/(\sqrt{\epsilon}+1)|^2$, and the electronic contribution to the dielectric constant $\epsilon_{el}$ can be written as:

$$\epsilon_{el} = 1 - \frac{(1-f)\omega_p^2}{\omega^2 + i\Gamma_2\omega} - \frac{f\omega_p^2}{\omega^2 + i\Gamma_1\omega}, \quad (3)$$

where f is the fraction of electron density related to the superconducting condensate (f=0 at $T \geq T_c$), $\omega_p$ is the plasma frequency, and $\Gamma_2$ and $\Gamma_1$ are effective collision frequencies for the normal and superconducting phases, respectively. The difference between the collision rates for the superconducting phase and the normal phase $\delta\Gamma = \Gamma_1 - \Gamma_2$ should be small compared to $\Gamma_1$ or $\Gamma_2$. Since no temperature dependence of the optical reflectivity of these materials in the energy range ~1.5 eV was earlier observed, we can assume that only $\delta\Gamma$ varies rapidly with temperature. The temperature dependence of the reflection coefficient following from Eq. (3) can be written in the form:

$$\frac{dR}{dT} = K\left[(1-f)\frac{d(\delta\Gamma)}{dT} - \delta\Gamma\frac{df}{dT}\right] \quad (4)$$

Figure 2:
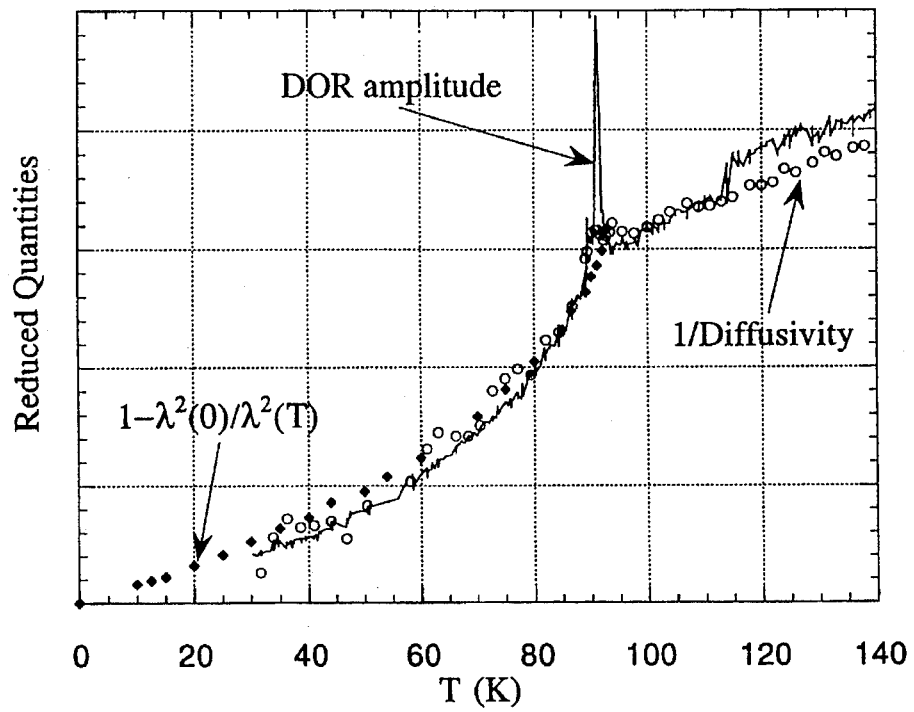
FIG. 2 is a comparison of the reduced temperature dependence of the differential optical response in the "a" polarization, thermal resistivity calculated from thermal diffusivity data, and normal phase density calculated from data for the penetration depth $\lambda$ using the formula $1-\lambda^2(0)/\lambda^2(T)$ for the normal phase density.

The smooth background is identified as a term $(1-f)d(\delta\Gamma)/dT$, proportional to the normal phase density, and the peak as proportional to $\delta\Gamma(df/dT)$, or superconducting phase response. Below $T_c$, the normal phase density can be determined independently from our diffusion measurements [I. M. Fishman et al., Phys. Rev. Lett. 72, 588 (1994), I. M. Fishman et al., Phys. Rev. B 50, 7192 (1994)] and from microwave penetration depth measurements [W. N. Hardy et al, Phys. Rev. Lett., 70, 3999 (1993)], and compared to the DOR data. This comparison is presented in FIG. 2. It will be seen that the thermal resistivity, the DOR background amplitude and the normal density have almost identical temperature dependence below $T_c$. The critical temperature is identified as the signal inflection point. Hence the DOR measurement provides a non-contact method for measurement of the critical temperature. Specific symmetry of the superconducting response (the peak in FIG. 1) allows to develop models for symmetry of the superconducting order parameter.

Figure 3:
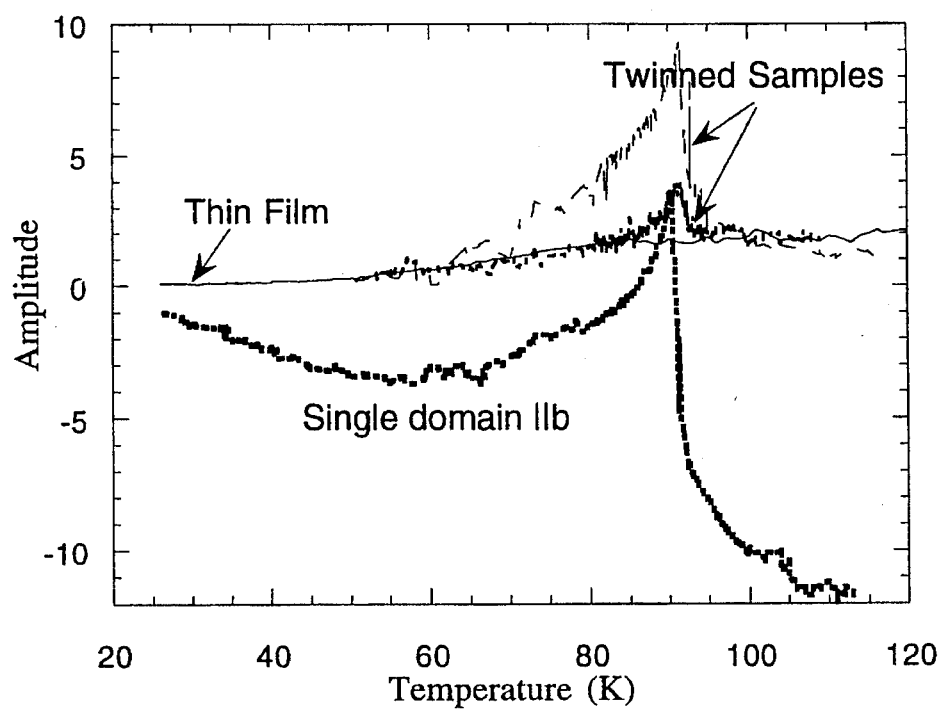
FIG. 3 is a comparison of differential optical responses of YBCO samples of different quality: single domains, twinned samples and thin films.

The results obtained for untwinned and twinned samples of different material quality are presented in FIG. 3. The measurement of twinned samples shows no angular anisotropy. The amplitude ratio of the background and the peak changes from sample to sample. For twinned samples, the background amplitude has the same sign as the peak. For low quality samples, the ratio of the peak to background signals is smaller than for high quality samples. In thin films (presumably, samples of lowest quality) the peak is hardly observable. The difference is explained by different ratio of $\delta\Gamma$, or optical loss difference between the normal and superconducting phases, and $d(\delta\Gamma)/dT$ for different samples. We make a conclusion that the correlation between the observed optical losses and the sample quality allows for independent non-contact optical evaluation of sample quality.

Figure 4:
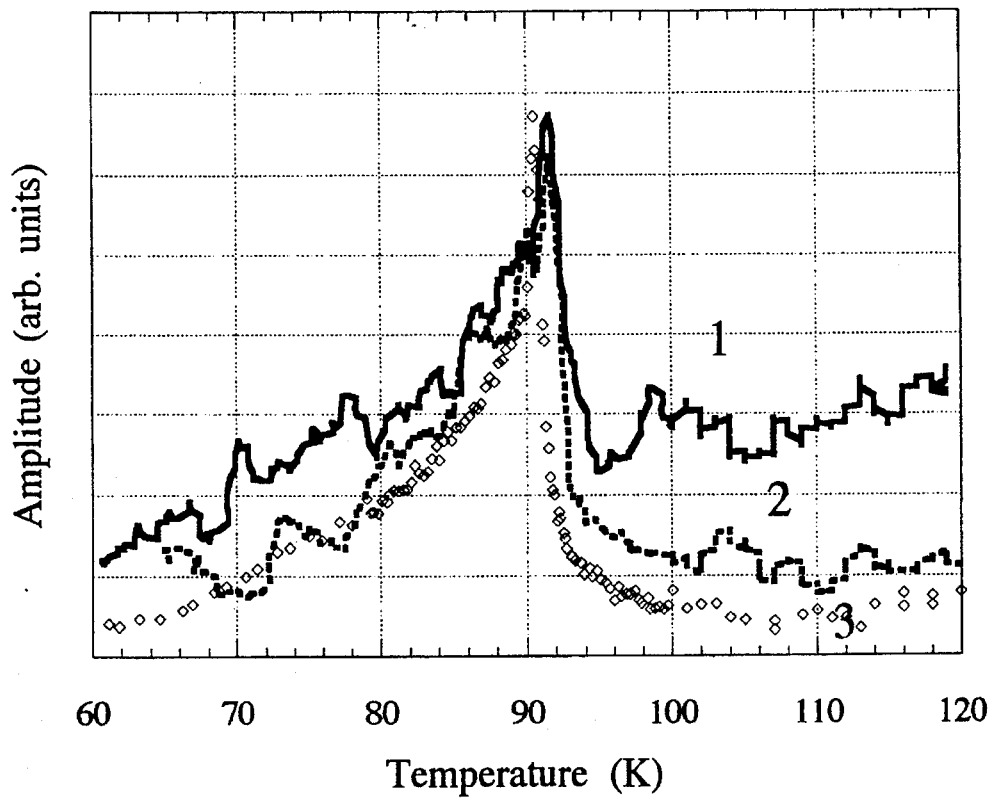
FIG. 4 presents crossed-polarized signals for the probe polarizations along a (curve 1) and b (curve 2) directions, compared with the peak component of curve 2 of FIG. 1.

Beyond measurements of the anisotropic DOR, the proposed method allows to investigate perturbation of the polarization state of the probe beam. This perturbation, especially non-reciprocal optical rotation, might have important consequences for theory of high-$T_c$ materials and for modern quantum theory of low-dimensional solids. To perform measurement of this perturbation, an additional polarizer has to be placed in front of the detector, and the crossed-polarized leaking signal has to be measured for several acute angles between the additional polarizer and polarization direction of the probe beam. For zero angle, the residual DOR signal should be observed. For non-reciprocal optical rotation, the crossed-polarized leaking signal measured for positive acute angles has to be different from the crossed-polarized leaking signal measured for negative acute angles. The residual DOR signal which passed through the polarizer orthogonal to the input beam probe polarization, for the input and output polarizations lined up with the a and b axes of the YBCO crystal, respectively, is shown in FIG. 4. The residual temperature dependent amplitude is one to two orders of magnitude less than the amplitudes of non-polarized signals. Far from $T_c$, virtually no signal passes through the analyzer. The results shown in FIG. 4 indicate that the superconducting transition is associated with a perturbation of the linear polarization state of the probe beam. Only the peak DOR component contributes to the crossed-polarized signals.

Figure 5:
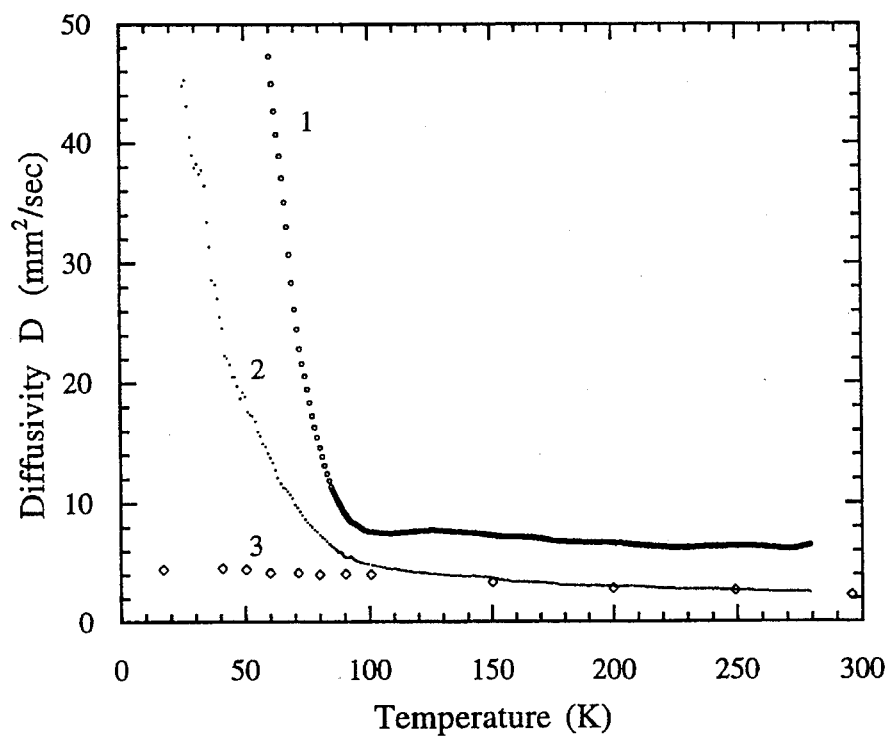
FIG. 5 presents YBCO thermal diffusivity as a function of temperature for a single domain (curve 1), across the twin boundary (curve 2), and in a thin film (curve 3).

Beyond the DOR, the thermal diffusivity in high-$T_c$ materials is also measured. For different high-$T_c$ samples, thermal diffusivity shows different temperature dependence below $T_c$ (FIG. 5). For high quality samples (curve 1), diffusivity grows over two orders of magnitude in the temperature range 40–93 K. For samples of lower quality, diffusivity grows less (curve 2). The thin film sample having presumably lowest quality shows very little change in diffusivity (curve 3).

Figure 6:
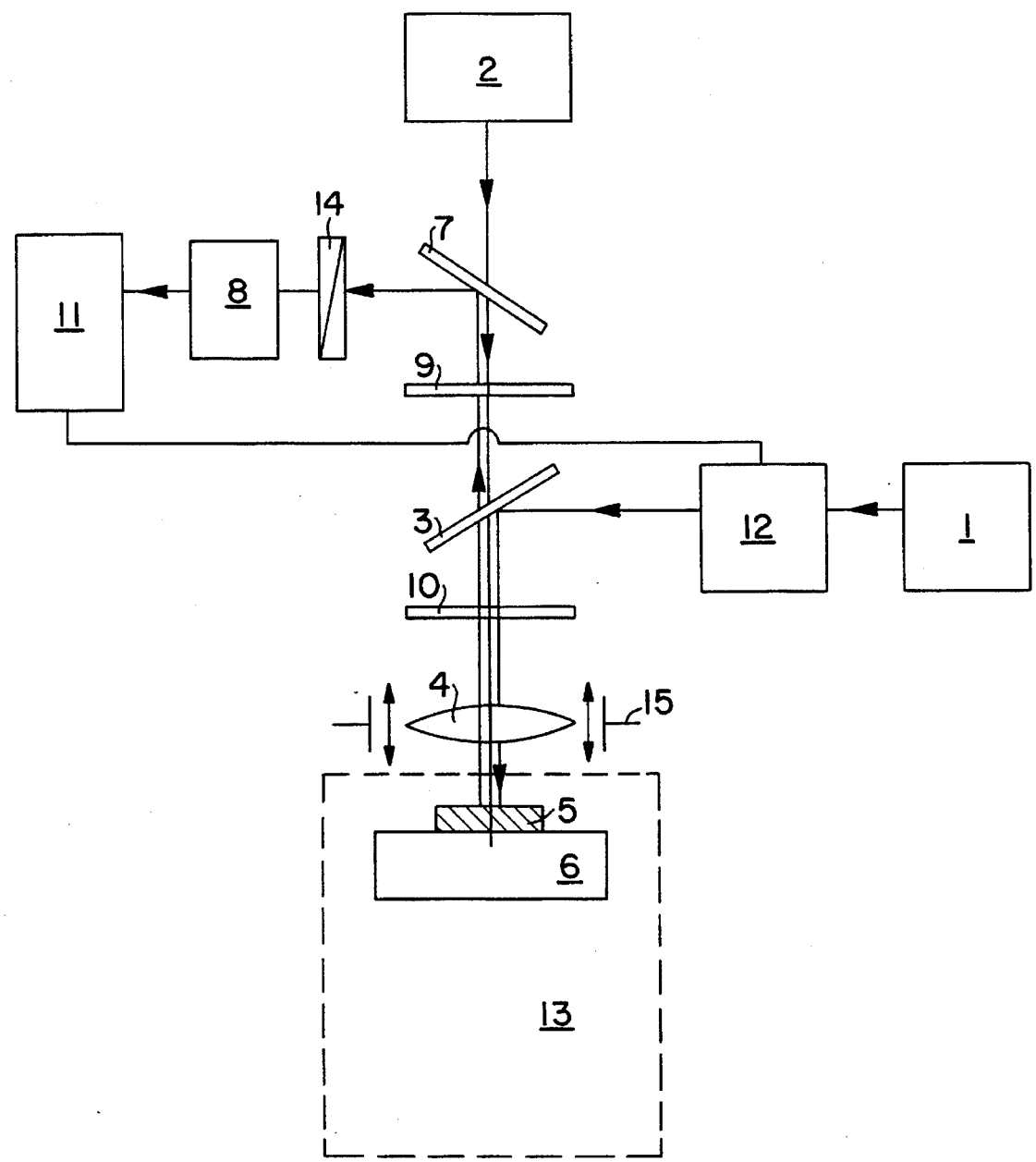
FIG. 6 is a schematic diagram of the apparatus used for investigation of the high-$T_c$ superconducting materials.

The described results demonstrate that the suggested method allows us to measure the material parameters essential for characterization of high-$T_c$ thin films and single crystals. To carry out the method of the subject invention in practice, an apparatus (DOR microscope) capable of measuring the DOR signal and thermal diffusivity of high-$T_c$ materials, has been developed. The apparatus is schematically presented in FIG. 6. It comprises two lasers: pump laser 1 and probe laser 2. As a pump source, a periodically modulated argon ion laser or a periodically modulated diode laser can be used. A CW diode laser can be used as a probe source to detect the reflectivity change caused by the thermal wave. Wavelengths of the laser sources should be separated by a spectral interval sufficient for optical isolation of the pump and probe beams in the microscope. Both beams are focused to several μm diameter spots on the sample surface. The laser beam powers at the sample are of the order of $10^{-5}$ W. The periodic temperature variation ΔT (peak-to-peak temperature modulation at the probe beam) varies in the limits of 0.1–10 K depending on the pump power. For a beam spacing of about 10 μm, ΔT is usually less than 0.2 K.

The beams from pump laser 1 and probe laser 2 are collimated and combined on beam splitter 3 and directed through objective focusing lens 4 onto the surface of sample 5. Sample 5 is positioned on a stage 6 for scanning purposes. The probe light beam is reflected off the surface of sample 5; the reflected light beam is then split off by beam splitter 7 and illuminates detector 8. The probe beam is linearly polarized. To orient the polarization vector in the sample surface and compensate for the polarization changes caused by the apparatus, polarization controller 9,10 is used. For example, half-wave plate 9 and quarter-wave plate 10 may be used in sequence, and the polarization at the sample is carefully calibrated as a function of the rotation of these plates. In another embodiment, the polarization of the probe beam stays unchanged, and to align the probe polarization, the sample is rotated about its normal. To determine the phase and amplitude of the probe signal relative to the pump, detector 8 and signal analyzer 11 are used. A semiconductor photodiode may be used as a detector. The detector output is compared with a reference signal from modulator 12 and analyzed by signal analyzer 11, for example a digital lock-in amplifier.

Figure 7:
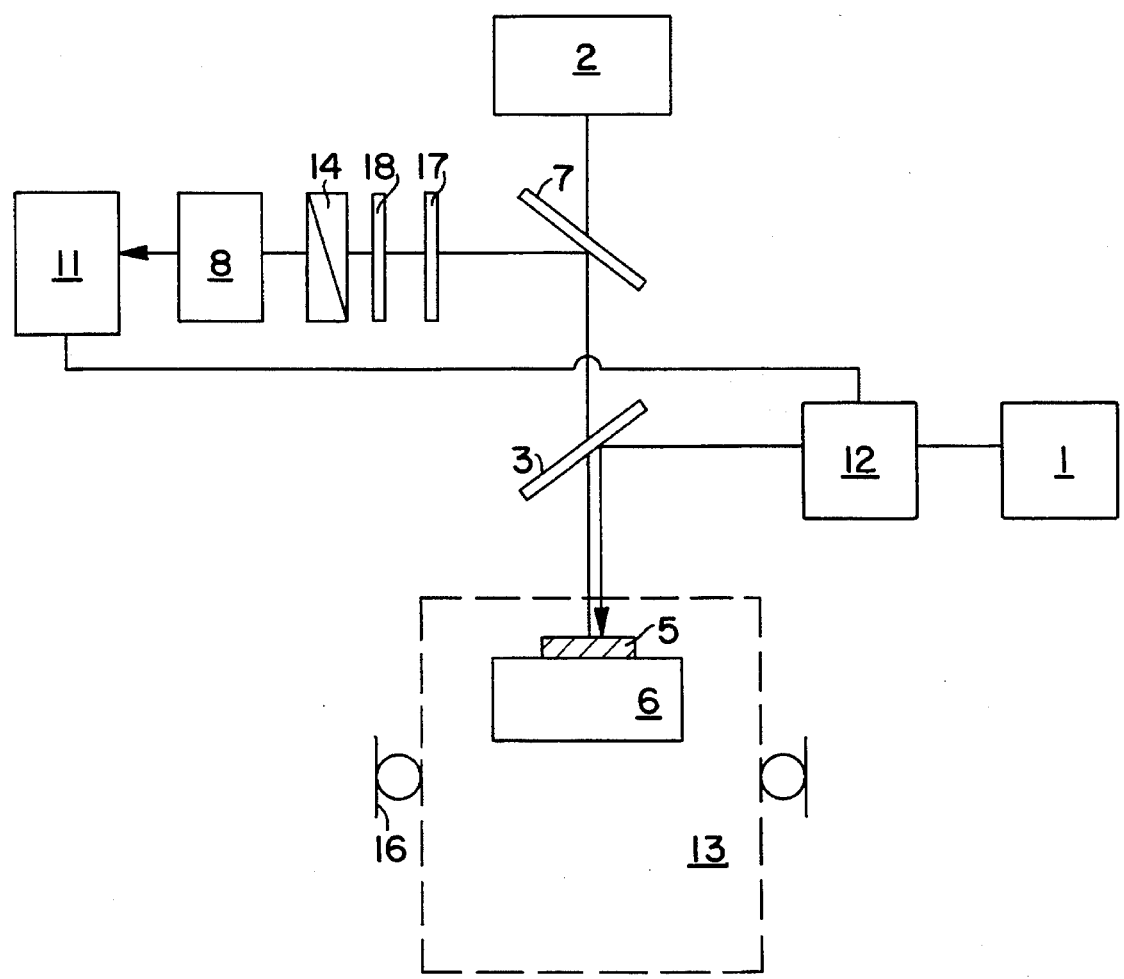
FIG. 7 is a schematic diagram of another embodiment of the apparatus used for investigation of the high-$T_c$ superconducting materials.

In the measurements described above, it is implied that temperature of the high-$T_c$ sample is varied in the temperature range including the critical temperature for the measured sample. To perform the sample cooling, ccooling means 13 are used, including an optical cryostat and a source of liquid helium (or liquid nitrogen if temperature is varied not lower than 77 K). We used a helium flow cryostat having a sample holder and a thin (0.1 mm) sapphire window. The window must be as thin as possible to avoid spherical aberrations of the optical beams. During the temperature cycling, the inner parts of the optical cryostat contract which causes defocusing and losing the field of view (the sample site where the measurements have started). To keep the sample in the focal plane of the objective, autofocusing electromechanical system 15 is used which provides a feedback to an error signal. If the sample moves out of the lens focal plane, the autofocusing system automatically compensates for this error. In the apparatus, the microscope objective lens is mounted in front of said material on a translation stage controlled by the error signal. To avoid the sample displacement in two orthogonal directions, the axis of the helium flow cryostat is positioned along the optical axis of said probe laser beam. Because the cryostat design is cylindrically symmetric, there is no off-axis displacement in the process of cooling. In another embodiment (FIG. 7), rotating means 16 are used to rotate cryostat 13 about its axis to align the probe polarization plane with different crystallographic axes of the sample, and the retardation plates 17,18 are positioned in front of the detector.

Although the invention has been described herein in its preferred form, those skilled in the art will recognize that many variations and modifications may be made thereto without departing from the spirit and scope of the invention. For example, different combinations of optical and mechanical elements may be used for relative orientation of the probe polarization vector and the high-$T_c$ sample and compensation for optical phase shift in mirrors, beamsplitters, etc. Also, different cooling devices, such as cryogenic refrigerators, liquid helium and liquid nitrogen dewars may be used as cooling means for sweeping the sample temperature.

What is claimed is:

1. A method for evaluation of high-$T_c$ superconducting material, comprising the steps of:

providing a periodic thermal excitation of said material and probing said material with a first polarized optical beam;

changing temperature of said material within a range including a critical temperature for said material; and measuring anisotropic differential optical reflectivity of said material as a function of said temperature and polarization of said first optical beam.

2. The method of claim 1, wherein the step of providing said periodic thermal excitation comprises the steps of:

generating a second optical beam with a pump laser;

modulating said second optical beam to attain a desired intensity modulation; and transmitting said modulated second optical beam onto a surface of said superconducting material.

3. The method of claim 2, wherein the step of probing said material with a first polarized optical beam comprises the steps of:

generating a first optical beam with a probe laser;

polarizing said first optical beam;

aligning a polarization direction of said first optical beam by rotating the plane of polarization of said first optical beam about an axis which is normal to said surface of said material;

transmitting said first optical beam onto said sample surface; and reflecting said first optical beam from said surface to a detector.

4. The method of claim 3, further comprising the step of analyzing a polarization state of said reflected first optical beam by an analyzer.

5. The method of claim 4, further comprising the step of obtaining an AC component of the intensity of said reflected first optical beam as a function of an angle between an axis of said analyzer and said polarization direction of said first optical beam.

6. The method of claim 5, wherein temperature of said material is changed by cryogenic means.

7. The method of claim 6, wherein anisotropic differential optical reflectivity value is defined by respective value of said AC component of intensity of said reflected first optical beam.

8. A method for evaluation of high-$T_c$ superconducting materials, comprising the steps of:

directing a first optical beam onto a surface of said material, said first beam being polarized;

aligning the plane of polarization of said first beam about an axis normal to said surface;

modulating intensity of a second optical beam and directing said second optical beam onto said surface of said material to obtain periodic thermal excitation thereon;

changing temperature of said material by cryogenic means within a range including a critical temperature for said material;

reflecting said first optical beam from said surface to a detector;

measuring anisotropic differential optical reflectivity of said material as a function of said temperature and said polarization of said first optical beam;

defining a crystallographic symmetry of said material by varying polarization of said first beam and obtaining anisotropic differential optical reflectivity for respective orientations of said plane of polarization; and defining a superconducting and a normal component responses of said material from comparison of differential optical reflectivities for different crystallographic orientations.

9. The method of claim 8, wherein said first and second optical beams are generated by a pump and probe lasers respectively.

10. The method of claim 9, further comprising a step of compensating depolarization of said reflected first optical beam introduced by anisotropic optical properties of said material and elements of an optical system.

11. The method of claim 10, wherein said step of compensating depolarization is provided by a retardation plate.

12. A method of measuring a critical temperature of a superconducting material comprising the steps of:

providing a periodic thermal excitation of said material and probing said material with a polarized optical beam;

changing temperature of said material within a range including a critical temperature for said material;

measuring anisotropic differential optical reflectivity as a function of said temperature and polarization of said material; and determining the critical temperature of said material by defining the inflection point of said differential optical reflectivity.

13. A method for evaluation of high-$T_c$ superconducting materials, comprising the steps of:

choosing a first sample of high-$T_c$ superconducting material with unknown optical losses;

directing a first optical beam onto a surface of said first sample, said first beam being polarized;

modulating intensity of a second optical beam and directing said second optical beam onto said surface of said first sample to obtain periodic thermal excitation thereon;

changing temperature of said first sample by cryogenic means within a range including a critical temperature for said first sample;

reflecting said first optical beam from said surface of said first sample to a detector;

measuring differential optical reflectivity of said first sample as a function of temperature;

defining a first ratio of amplitudes of normal and superconducting responses of said first sample;

choosing a second sample of high-$T_c$ superconducting material having predetermined optical losses;

measuring differential optical reflectivity of said second sample as a function of said temperature;

defining a second ratio of amplitudes of normal and superconducting responses of said second sample; and defining optical quality of said first sample by comparing said first ratio of amplitudes of normal and supercondicting responses of said first sample to said second ratio of amplitudes of normal and supercondicting responses of said second sample.

14. A method for evaluation of high-$T_c$ superconducting materials, comprising the steps of:

directing a first optical beam onto a surface of said material, said first beam being polarized;

modulating intensity of a second optical beam and directing said second optical beam onto said surface of said sample to obtain periodic thermal excitation thereon;

changing temperature of said material within a range including a critical temperature for said material;

reflecting said first optical beam from said surface to a detector;

positioning a polarizer in front of said detector normal to a polarization direction of said first optical beam;

measuring residual differential optical reflected signal of said sample as a function of temperature;

rotating said polarizer by a positive acute angle from a normal to the polarization direction of said first optical beam;

measuring a first leaking differential optical reflectance signal of said sample as a function of temperature;

rotating said polarizer by a negative acute angle from the normal to the polarization direction of said first optical beam;

measuring a second leaking differential optical reflectance signal of said sample as a function of temperature; and evaluating temperature-induced optical rotation as a ratio of said first to said second leaking differential optical reflectance signals.

15. A method for evaluation of high-$T_c$ superconducting materials comprising the steps of:

focusing a first modulated laser beam onto a surface of said material;

focusing the second laser beam onto said surface of said material with a predetermined distance between focal spots of said first and second beams;

reflecting said second laser beam from said surface to a detector;

obtaining an AC component of the intensity of said reflected second laser beam;

changing temperature of said superconducting material by cryogenic means;

measuring temperature dependence of phase of said AC component; and obtaining thermal diffusivity of said material from said temperature dependence.

16. An apparatus for evaluation of high-$T_c$ superconducting sample, comprising:

a heat source for periodically heating said sample;

a probe laser for illuminating said sample by an incident light beam, said incident light beam being polarized;

a polarization controller for controlling a state of polarization of said incident light beam of said probe laser and analyzing a state of polarization of a light beam reflected from said sample;

a detector for measuring a periodic component of intensity of said reflected light beam; and cooling means with said sample disposed therein.

17. The apparatus of claim 16, wherein said source is a pump laser which emits a light beam.

18. The apparatus of claim 17, wherein an axis of said cooling means is aligned with an axis of said incident beam.

19. The apparatus of claim 18, wherein said cooling means is a flow helium cryostat having a sample holder and an optically transparent window positioned normal to said incident beam axis and said cooling means axis.

20. The apparatus of claim 19, wherein said polarization controller comprises:

means for rotating a polarization plane of said polarized incident light beam; and a polarizer for analyzing said reflected light beam, said polarizer positioned in front of said detector.

21. The apparatus of claim 20, further comprising a beamsplitter for combining said light beams of said pump laser and said probe laser.

22. The apparatus of claim 21, wherein said means for rotating is a half-wave plate.

23. The apparatus of claim 22, further comprising a quarter-wave plate for compensating depolarization of said probe laser beam, said quarter-wave plate interposed between said half-wave plate and said beamsplitter.

24. The apparatus of claim 23, further comprising an objective lens for focusing of said probe laser beam, said objective lens mounted in front of said sample.

25. The apparatus of claim 24, further comprising an autofocusing system for retaining said sample in the focal plane of said objective lens.

26. The apparatus of claim 19, wherein said polarization controller comprises:

means for rotating said sample about its normal axis; and means for rotating a polarization plane of said reflected light beam.

27. The apparatus of claim 19, wherein said polarization controller comprises means for rotating said cooling means about said cooling means axis.

* * * * *